United States Patent [19]

Moeschler et al.

[11] Patent Number: 4,762,716

[45] Date of Patent: * Aug. 9, 1988

[54] PURE ANNONIN AND A PROCESS FOR THE PREPARATION THEREOF

[75] Inventors: Heinrich F. Moeschler, Cologne; Wolfgang Pflüger, Leichlingen; Detlef Wendisch, Bergisch-Gladbach, all of Fed. Rep. of Germany

[73] Assignee: Bayer Aktiengesellschaft, Leverkusen, Fed. Rep. of Germany

[*] Notice: The portion of the term of this patent subsequent to Aug. 25, 2004 has been disclaimed.

[21] Appl. No.: 65,196

[22] Filed: Jun. 22, 1987

Related U.S. Application Data

[63] Continuation of Ser. No. 785,181, Oct. 7, 1985, Pat. No. 4,689,282.

[30] Foreign Application Priority Data

Oct. 23, 1984 [DE] Fed. Rep. of Germany ....... 3438763

[51] Int. Cl.$^4$ ............................................. A61K 35/78
[52] U.S. Cl. ........................... 424/195.1; 424/DIG. 10
[58] Field of Search ..................... 424/195.1, DIG. 18

[56] References Cited

U.S. PATENT DOCUMENTS 4,689,232  8/1987  Moeschler et al. .............. 424/195.1

OTHER PUBLICATIONS

Biological Abst. 65: 63326, 1978.

*Primary Examiner*—John Rollins
*Attorney, Agent, or Firm*—Sprung Horn Kramer & Woods

[57] ABSTRACT

Annonin, a substantially pure insecticidally active compound obtained by extracting comminuted *Annona squamosa* parts to remove the petroleum ether solubles, then optionally extracting with alcohol to dissolve the desired material, then extracting either the petroleum ether-residue or the alcohol extract with an aliphatic halogenohydrocarbon, an aliphatic ether and/or an ester, and discarding the residue, and evaporating off the solvent. It has the IR spectrum shown in the drawing.

4 Claims, 1 Drawing Sheet

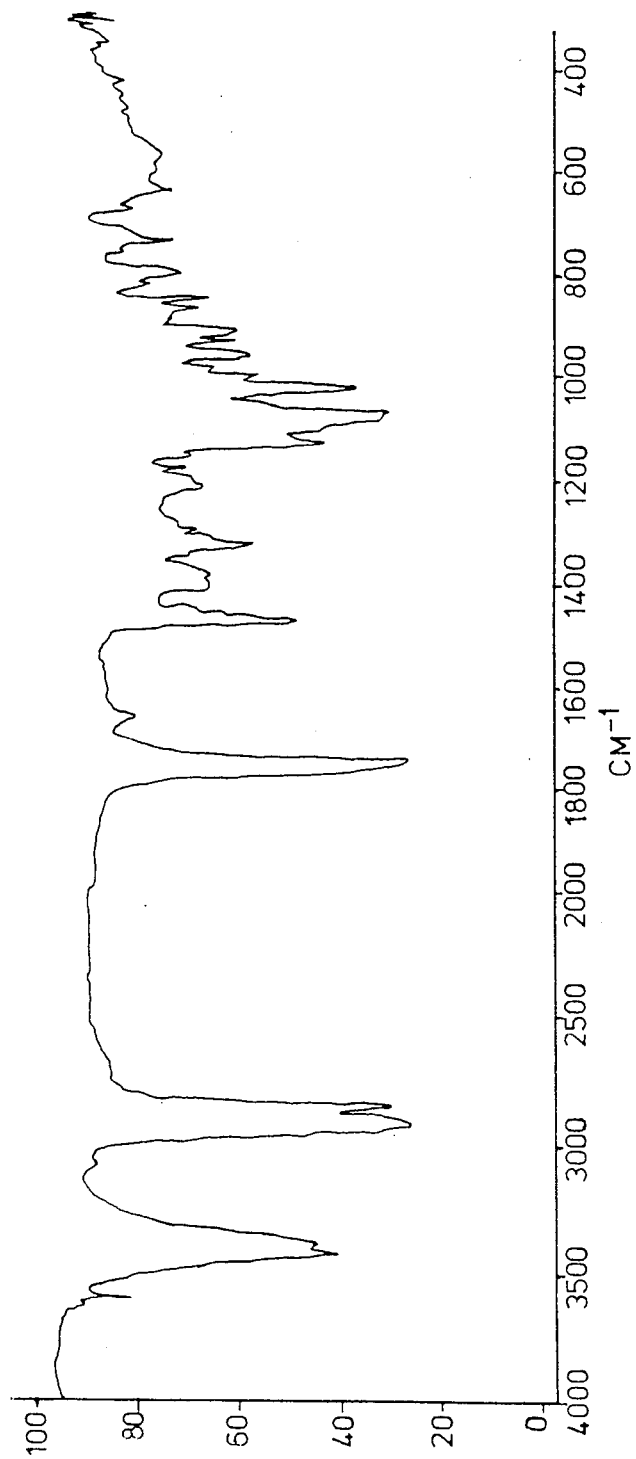

PURE ANNONIN AND A PROCESS FOR THE PREPARATION THEREOF

This is a continuation, of application Ser. No. 785,181, filed Oct. 7, 1985, now U.S. Pat. No. 4,689,232.

The present invention relates to a new organochemical compound from the custard apple tropical plant Annona squamosa, family Annonaceae, a process for its isolation and its use as an insecticide. The new compound is called annonin below.

It has already been disclosed that extracts from species of Annona have certain insecticidal properties. However, the activity of these extracts is not always satisfactory for practical purposes (compare Journal of Economic Entomology, Volume 76, No. 3, pages 573-576 (1983)).

The new organochemical compound (name: annonin) which can be characterized as follows has been found:

1. Appearance: Colorless amorphous waxy solid.
2. Solubility: The waxy substance is insoluble or very sparingly soluble in petroleum ether and water and readily soluble in ether, $CHCl_3$, $CH_2Cl_2$, methanol and ethyl acetate. It exhibits a positive reaction with vanillin/sulphuric acid and Dragendorff's reagent, although it contains no nitrogen.
3. Molecular weight (MW): 622

The MW was determined by:

FD mass spectrum: m/e 623 ($M^+ +H$)

DCI " " : m/e 623 ($M^+ +H$) (with isobutane as the reactant gas)

EI mass spectrum: m/e 604 as the highest fragmentation with an elemental composition, determined by the fine mass: $C_{37}H_{64}O_6 (=MW-H_2O)$.

4. Elemental analysis: C=70.5%; H=10.7%; O=18.1% found, C=71.34%; H=10.68%; O=17.98% calculated.

Empirical formula (MW=622): $C_{37}H_{66}O_7$.

5. UV spectrum:

$\lambda$ max acetonitrile = 209 nm ($\epsilon_{max}$ 9,500).

6. IR spectrum (KBr) $\gamma$ max: 3,420; 3,380; 2,920; 2,850; 1,745; 1,655; 1,465; 1,320; 1,120; 1,070; 1,020; 960; 930; 910; 860; 840; 740; 630 cm$^{-1}$ (compare the figure).

7. EI mass spectrum: m/e (intensity) 604 (<1)=$C_{37}H_{64}O_6$; 586 (<1); 568 (<1); 519 (1.3); 501 (2.8); 483 (2.7); 465 (1.5); 417 (6.9); 399 (16.7)=$C_{26}H_{39}O_3$; 347 (62.7)=$C_{22}H_{35}O_3$; 329 (14.7); 319 (15); 295 (100)=$C_{18}H_{31}O_3$ (base peak); 267 (19); 239 (19.3)=$C_{15}H_{27}O_2$; 203 (8); 195 (14); 169 (18); 135 (22); 121 (32.7); 109 (39.3); 97 (49.3); 95 (66); 83 (34.3); 81 (60); 71 (44); 69 (38.7); 67 (46); 57 (27.3); 55 (56); 43 (35.3); 41 (35).

8. $^{13}$C-NMR spectrum: (CDCl$_3$) $\delta$ (ppm): 173.897 (0-CO-; $\alpha,\beta$-unsaturated), 148.879 (olefinic CH), 134.329 (olefinic C), 83.379 (CH, $\alpha$ to 0), 82.869 (CH, $\alpha$ to 0), 82.546 (CH, $\alpha$ to 0), 82.197 (CH, $\alpha$ to 0), 77.338 (CH, $\alpha$ to 0 and CH3), 74.127 (CH, $\alpha$ to 0), 71.657 (CH, $\alpha$ to 0), 71.320 (CH, $\alpha$ to 0), 37.413 (CH$_2$), 37.207 (CH$_2$), 33.108 (CH$_2$), 32.397 (CH$_2$), 31.789 (CH$_2$), 29.696 (CH$_2$), 29.541 (3xCH$_2$), 29.518 (CH$_2$), 29.438 (CH$_2$), 29.321 (CH$_2$), 29.233 (CH$_2$), 29.106 (CH$_2$), 28.910 (CH$_2$), 28.891 (CH$_2$), 28.400 (CH$_2$), 27.328 (CH$_2$), 25.597 (CH$_2$, allyl.), 25.573 (CH$_2$), 25.097 (CH$_2$), 24.723 (CH$_2$), 22.552 (CH$_2$, $\alpha$ to CH$_3$), 21.981 (CH$_2$), 19.145 (CH$_3$, $\alpha$ to CH), 14.007 (CH$_3$, $\alpha$ to CH$_2$).

9. $^1$H-NMR spectrum: (CDCl$_3$) $\delta$ (ppm): 6.988 (olefinic H, pseudo q), 4.995 (CH, $\alpha$ to 0 and CH$_3$; pseudo qq), 3.97-3.77 (5 CH, $\alpha$ to 0), 3.600 (CH, $\alpha$ to 0, m), 3.400 (CH, $\alpha$ to 0, pseudo q), 2.263 (allyl CH$_2$, pseudo tt), 2.05-1.18 (23 CH$_2$, complex), 1.405 (CH$_3$, $\alpha$ to 0 and CH, d, J=6.5 Hz), 0.878 (CH$_3$,$\alpha$ to CH$_2$, t, J=6.6 Hz) 3 hydroxyl-H at about 3, broad.

10. Optical rotation (C=0.15 in $CH_2Cl_2$):

| nm | 589 | 578 | 546 | 436 | 365 | 302 |
|---|---|---|---|---|---|---|
| $[\alpha]_{25}$ | +21.5 | +21.6 | +29.8 | +51.3 | +89.5 | +182.6 |

11. Circular dichroism: 239 nm ($\Delta\epsilon -0.55$); 210 nm ($\Delta\epsilon +5.70$) (in methanol).

12. EI mass spectrum of trioxoannonin: m/e (intensity) (prepared from annonin by oxidation with Jones reagent) 616, molecular ion (10); 598 (5); 488 (2); 433 (25); 415 (98); 397 (12); 389 (3); 387 (3); 371 (3); 363 (1); 345 (2); 337 (3); 323 (32); 305 (58); 293 (24); 287 (17); 279 (12); 265 (8); 261 (8); 237 (4); 195 (16); 183 (17); 177 (19); 175 (10); 167 (12); 155 (20); 153 (12); 151 (14); 149 (12); 147 (12); 145 (10); 143 (16); 125 (16); 123 (17); 121 (18); 113 (40); 111 (22); 109 (23); 107 (26); 99 (20); 97 (34); 95 (45); 85 (25); 83 (32); 81 (41); 71 (56); 69 (46); 67 (38); 57 (46); 55 (33); 43 (96); 41 (52); 32 (>100), 28 (>100); 18 (>100); 17 (>100).

In the drawing, the figure is the IR spectrum of annonin.

It has been found that the new compound annonin has biological properties which enable it to be used as an agent for combating pests, preferably as an insecticide.

It has furthermore been found that the new compound annonin is obtained by a process in which, using the comminuted plant parts, preferably the seeds, of Annona squamosa.

(1) the contents which are soluble in petroleum ether are extracted and the petroleum ether extract is discarded, and (2) the plant material which has been largely freed from the substances which are soluble in petroleum ether is then either (a) extracted with water-miscible alcohols, if appropriate in the presence of water, the residue is discarded, the extract is concentrated and the concentrated extract obtained in this manner is extracted with an aliphatic halogenohydrocarbon, an aliphatic ether and/or an ester and the residue is discarded, or (b) extracted with an aliphatic halogenohydrocarbon, an aliphatic ether and/or an ester and the residue is discarded, (3) the crude annonin obtained according to (a) or (b) is isolated by evaporating off the solvent and, if appropriate, (4) is purified by customary methods.

For use as an agent for combating pests, it is in many cases not necessary further to purify the crude annonin obtained according to (3).

Fresh or dried, preferably fresh, seeds from Annona squamosa fruits can be employed for the process according to the invention for isolating annonin, it also being possible for the seeds or the comminuted seed material to be prepared so that decay is prevented (for example by deep-freezing, sterilization and the like).

In carrying out the process according to the invention, the seeds are comminuted by customary methods, for example mechanically by crushing, chopping or grinding, and the comminuted seed mass is first exhaustively defatted with hydrocarbon mixtures, such as petroleum ether, or with defined hydrocarbons, such as pentane or hexane, preferably petroleum ether (30° to 60° C.), by extraction by customary methods. This process can be carried out at room temperature or elevated temperature, the temperature being determined by the boiling point of the solvent, and preferably being between room temperature and 60° C. The extraction can be carried out discontinuously or continuously, for example in a stirred kettle, in a Soxhlet or in a percolator.

This extract preferentially contains the strongly lipophilic compounds contained in the seed and is discarded.

The seed mass thus treated is extracted in the next step several times with an aliphatic alcohol with 1 to 3 carbon atoms or with alcohol/water mixtures, such as methanol/water, ethanol/water or propanol/water in various ratios; mixtures such as methanol/water (90:10 to 10:90) or ethanol/water (80:20 to 20:80) and methanol and/or ethanol without the addition of water are preferred.

The extraction can be carried out either at room temperature or at elevated temperature (preferably 15° to 70° C., in particular 30° to 60° C.), advantageously with stirring. In addition to discontinuous extraction, continuous extraction, for example in a Soxhlet or in a percolator, is also possible.

The extract obtained in this manner is concentrated in vacuo until most of the alcohol has been removed, and is then taken up in polar organic solvents which are sparingly miscible with water, such as a chlorohydrocarbon, for example $CH_2Cl_2$ or $CHCl_3$, or an aliphatic ether, such as diethyl ether, or an ester of a lower aliphatic alcohol and a lower aliphatic acid, such as ethyl acetate, or a mixture of these solvents. After the solvent has been evaporated off (preferably under reduced pressure), a concentrate is obtained which contains the annonin according to the invention as the main component.

It is also possible to dispense with the extraction with alcohol or alcohol/water and to subject the plant material, which has been largely freed from substances which are soluble in petroleum ether, directly to extraction with a chlorohydrocarbon, ether and/or ester. The residue is discarded and the solvent is evaporated off, a concentrate being obtained which contains annonin as the main component.

Further purification which may be desired can be carried out in accordance with customary methods by chromatography, for example in the form of column chromatography or preparative thin layer chromatography. Examples of suitable carrier materials for this are aluminium oxide, silica gel, magnesium silicate, active charcoal, cellulose or dextran gels and derivatives of polyamides, such as acetylated polyamide. Mobile phases which can be used both in the preparative thin layer chromatography and in the column chromatography are those solvents or solvent mixtures in which the substance according to the invention is soluble. Examples of suitable solvents are ethers, such as diethyl ether, halogenated aliphatic hydrocarbons, such as chloroform and methylene chloride, esters, such as ethyl acetate, lower aliphatic alcohols, such as methanol, ethanol, n-propanol and isopropanol, or mixtures of these solvents, it also being possible, if appropriate, to add small amounts of n-hexane, n-pentane or petroleum ether.

Mixtures of chloroform or methylene chloride and methanol are preferably used. If, for example, silica gel is employed as the carrier material, the further purification of the concentrate can be particularly advantageously carried out with a stepwise gradient of $CHCl_3$ and methanol. In this case, a silica gel which has been deactivated with up to 10% of water, preferably a silica gel which has been deactivated with 5 to 10% of water, is preferably used for the chromatography, it also being possible to use silica gel which has not been deactivated in this manner.

The elution is advantageously started with $CHCl_3$ to which up to 15% of methanol is added stepwise. The active compound according to the invention can preferably be eluted with chloroform containing 2.5 to 5% of methanol.

Further purification of the active compound according to the invention can advantageously be effected by preparative HPLC on a RP-18 column with different mobile phases. Suitable mobile phases are mixtures of methanol/acetonitrile and water, containing methyl tert.butyl ether and propionitrile.

All the % data given in the description (including the examples) relate to percentages by weight, unless indicated otherwise. All the ratio data (for example in the solvent mixtures) relate to parts by volume (vol/vol), unless otherwise indicated.

The active compound is well tolerated by plants and are suitable for combating animal pests, especially insects, which are encountered in agriculture, in forestry, in the protection of stored products and of materials, and in the hygiene field. It is active against normally sensitive and resistant species and against all or some stages of development. An acute and/or development-retarding and development-inhibiting action manifests itself, depending on the species of insect and the concentration of active compound. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Neohotettix cincticeps,*

*Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp.. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The phytoparasitic nematodes include Pratylenchus spp., *Radopholus similis, Ditylenchus dipsaci, Tylenchulus semipenetrans,* Hederodera spp., Meloidogyne spp., Aphelenchoides spp., Longidorus spp., Xiphinema spp. and Trichodorous spp..

The active compound can be converted to the customary formulations, such as solutions, emulsions, suspensions, powders, foams, pastes, granules, aerosols, natural and synthetic materials impregnated with active compound, very fine capsules in polymeric substances and in coating comoositions for seed, and formulations used with burning equipment, such as fumigating cartridges, fumigating cans, fumigating coils and the like, as well as ULV cold mist and warm mist formulations.

These formulations are produced in known manner, for example by mixing the active compound with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention can be present in its commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compound according to the invention can furthermore be present in its commercially available formulations and in the use forms, prepared from these formulations, as a mixture with synergistic agents. Synergistic agents are compounds which increase the action of the active compound, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compound is employed in a customary manner appropriate for the use forms.

When used against hygiene pests and pests of stored products, the active compound is distinguished by an excellent residual action on wood and clay as well as a good stability to alkali on limed substrates.

The preparation of the active compound according to the invention may be illustrated with the aid of the following examples:

EXAMPLE 1

Extraction of the seeds of *Annona squamosa* (500 g scale)

500 g of fresh seeds (deep-frozen) of Annona squamosa (origin: Thailand) are comminuted in a mixing apparatus with a knife unit, without the addition of liquid.

The comminuted seeds are extracted by stirring at 30° C. 7 times, for 30 minutes each time, with 800 ml of petroleum ether or pentane each time. The extracts are discarded.

The seed mass which has been filtered off and has been defatted in this manner is then extracted by stirring at 60° C. 5 times with 500 ml of ethanol/$H_2O$ (80:20) each time and the solid components are filtered off.

After the ethanol has been stripped off, an oily residue which is partly suspended or emulsified in water (depending on the residual content of ethanol) is obtained. This residue is extracted exhaustively (5 times with 500 ml each time) with ether. The ether phase is separated off. After the ether phase has been concentrated, 1.8 g of a waxy mass enriched in the insecticidal main component annonin are obtained. "Ether" in this example denotes diethyl ether.

EXAMPLE 2

Extraction of the seeds of *Annona squamosa* (22 kg scale)

22 kg of fresh seeds of Annona squamosa (origin: Thailand) are comminuted in a mixing apparatus with a knife unit. The seed mass is extracted by stirring 6 times with a total of 191 l of petroleum ether at 30° C. in a stirred kettle and the petroleum ether solution is discarded.

The seed mass which has been filtered off is dried in vacuo and comminuted again with the mixing apparatus (10.45 kg). It is extracted a total of 5 times with 36 l of ethanol/$H_2O$ (80:20) each time, in a stirred kettle at 60° C., and the solids are filtered off.

The 180 l of filtrate are concentrated (stripping off of the ethanol). 18 l of oil are obtained which, after drying under a high vacuum, gives a yield of 0.91 kg of crude product.

EXAMPLE 3

Column chromatography on silica gel (enrichment)

9 g of the extract obtained in Example 1 are dissolved in 25 ml of chloroform and the solution is applied to a silica gel column (70 mm $\phi \times$ 700 mm long) deactivated with 10% of $H_2O$.

Elution is effected in stepwise gradients ($\bar{v}=3$ ml/minute) with $CCl_3$/MeOH:

| Amount of eluate | $CHCl_3$/MeOH (vol/vol) | Fraction |
| --- | --- | --- |
| 2.25 l | 97.5/2.5 | 1–50 |
| 1.35 l | 95/5 | 51–80 |

The active compound according to the invention (annonin) is eluted in fractions 37 to 60.

After the solvent has been stripped off, 3.1 g of a waxy mass are obtained.

EXAMPLE 4

Isolation of annonin (fine purification)

200 mg of the product obtained in Example 3 are separated over a preparative HPLC column (570 mm x 30 mm $\phi$) filled with LiChroprep (RP 18, Merck ®). Mobile phase (vol/vol): methanol (700), $H_2O$ (300), methyl tert.-butyl ether (150), propionitrile (2.5) detector: UV flow cell, 220 nm.

The flow is 15 ml/minute. The fractions containing annonin are combined and freed from the solvent in vacuo. 85 mg of annonin are obtained.

The biological activity of the compound according to the invention may be illustrated with the aid of the following examples:

EXAMPLE A

Phaedon test

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage plants (*Brassica oleracea*) are treated with the preparation of the active compound of the desired concentration. A leaf of the treated plants is placed in a plastic container and infested with mustard beetle larvae (*Phaedon cochleariae*). After 2 and 4 days, in each case another leaf from the same plant is used for subsequent feeding.

After the specified periods of time, the destruction in % is determined. 100% means that all the larvae have been killed; 0% means that none of the larvae have been killed.

In this test, for example, Phaedon larvae are destroyed to the extent of 100% after 14 days, at a concentration of 0.004%.

EXAMPLE B

Plutella test

Solvent: 3 parts by weight of acetone
Emulsifier: 1 part by weight of alkylaryl polyglycol ether To produce a suitable preparation of active compound, 1 part by weight of active compound is mixed with the stated amount of emulsifier, and the concentrate is diluted with water to the desired concentration.

Cabbage plants (*Brassica oleracea*) are treated with the preparation of the active compound of the desired concentration. A leaf of the treated plants is placed in a plastic container and infested with cabbage moth caterpillars (*Plutella maculipennis*). After 2 and 4 days, in each case another leaf from the same plant is used for subsequent feeding.

After the specified periods of time, the destruction in % is determined. 100% means that all the caterpillars have been killed; 0% means that none of the caterpillars have been killed.

In this test, for example, Plutella larvae are destroyed to the extent of 100% after 14 days, at a concentration of 0.004%.

EXAMPLE C

Myzus test

Solvent: 3 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Broad beans (*Vicia faba*) are infested with aphids (*Myzus persicae*) and treated with the preparation of active compound of the desired concentration. After 2, 6 and 10 days, the inhibition of the aphid population is rated in % action. 100% means that all the aphids have been killed; 0% means that the preparation had no effect.

In this test, for example, an effect of 98% was found after 10 days, at a concentration of 0.004%.

Conditions for recording the spectra

All the $^{13}$C-experiments of a one- and two-dimensional type were carried out at 50.3 MHz on an XL-200 spectrometer (Varian, Palo Alto/USA). One-dimensional proton measurements were carried out with and without pulsed homo-decoupling at 360 MHz on a WH-360 spectrometer (Bruker, Rheinstetten/FRG) with an Aspect 2000 computer. $^1$H-Cosy experiments were carried out at 200 MHz on the XL-200 spectrometer. The solvent was in all cases CDCl$_3$, which was also used as the $^2$H-lock substance. Tetramethylsilane was used as the standard in all cases.

The EI mass spectrum was determined with a Finnigan-MAT CH7 spectrometer with an SS 220 data system, with vaporisation regulated by total ion flow.

Explanation of the abbreviations and trademarks

TLC = thin layer chromatography
HPLC = high pressure liquid chromatography
FD = field desorption
DCI = direct chemical ionisation
EI = electron ionisation
RP 18: silica gel silanized with a C-18 carbon chain, for reversed phase chromatography
LiChroprep (RP 18): silica gel silanised with a C-18 hydrocarbon chain for reversed phase chromatography LiChroprep = trademark of E. Merck, Darmstadt, Federal Republic of Germany Explanation of FIG. 1

FIG. 1 shows the IR spectrum of annonin. In this figure, the ordinate denotes the transmission in % and the abscissa denotes the wavelength in cm$^{-1}$.

It will be understood that the specification and examples are illustrative but not limitative of the present invention and that other embodiments within the spirit and scope of the invention will suggest themselves to those skilled in the art.

We claim:

1. A process for the preparation of pure annonin comprising
   (a) comminuting parts of *Annona squamosa*,
   (b) extracting the parts with petroleum ether and discarding the petroleum ether extract to leave an annonin-containing material,
   (c) extracting the annonin-containing material with an aliphatic halogenohydrocarbon, an aliphatic ether, an ester, or mixtures thereof and discarding the residue, and
   (d) evaporating off the solvent.

2. The process according to claim 1, wherein the annonin-containing material of (b) is extracted with a water-miscible alcohol to dissolve the annonin, and the alcohol extract of annonin is extracted in (c).

3. The process according to claim 2, wherein the alcohol extraction is effected in the presence of water.

4. The process according to claim 1, wherein the plant parts are the seeds.

* * * * *